United States Patent [19]

Cue, Jr. et al.

[11] 4,435,578

[45] Mar. 6, 1984

[54] SORBINIL BY OPTICAL RESOLUTION OF PRECURSOR 6-FLUORO-4-UREIDOCHROMAN-4-CARBOXYLIC ACID

[75] Inventors: Berkeley W. Cue, Jr., Gales Ferry; Bernard S. Moore, Waterford, both of Conn.

[73] Assignee: Pfizer Inc., New York, N.Y.

[21] Appl. No.: 440,641

[22] Filed: Nov. 10, 1982

[51] Int. Cl.³ ............... C07D 491/107; C07D 311/68
[52] U.S. Cl. ..................................... 548/309; 549/404
[58] Field of Search ....................... 549/404; 548/309

[56] References Cited

U.S. PATENT DOCUMENTS 4,117,230  9/1978  Sarges ................................ 548/309
4,130,714 12/1978  Sarges ................................ 548/309
4,286,098  8/1981  Sarges ................................ 548/309
4,348,526  9/1982  Sarges ................................ 548/309

Primary Examiner—Nicky Chan
Attorney, Agent, or Firm—Charles J. Knuth; Albert E. Frost; Robert K. Blackwood

[57] ABSTRACT

Sorbinil is obtained by cyclization of S-6-fluoro-4-ureidochromane-4-carboxylic acid, which is in turn obtained by resolution of racemic 6-fluoro-4-ureidochroman-4-carboxylic acid via diasteromeric salts with either D-(+)-(1-phenethyl)amine or L-(−)-ephedrine.

8 Claims, No Drawings

SORBINIL BY OPTICAL RESOLUTION OF PRECURSOR 6-FLUORO-4-UREIDOCHROMAN-4-CARBOXYLIC ACID

BACKGROUND OF THE INVENTION

S-6-Fluorospiro[chroman-4,4'-imidazolidine]-2',5'-dione, also named S-2,3-dihydro-6-fluorospiro[4H-1-benzopyran-4,4'-imidazolidine]-2',5'-dione (U.S.A.N.: sorbinil) of the formula

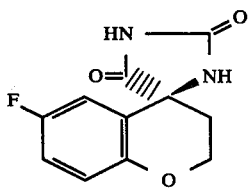

is a highly potent aldose reductase inhibitor having especial value in effectively controlling the chronic complications of diabetes mellitus. (Sarges, U.S. Pat. No. 4,130,714). The present invention concerns an improved process for preparing sorbinil and intermediates used in this improved process.

Heretofore, sorbinil was prepared by resolution of the corresponding racemic 6-fluorospiro[chroman-4,4'-imidazolidine]-2',5'-dione, of the formula

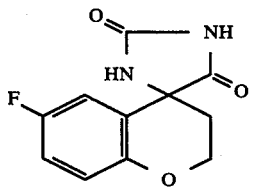

by using highly toxic brucine as the resolving agent in high volumes of solvent (U.S. Pat. No. 4,130,714).

Surprisingly, we have found that resolution of precursor 6-fluoro-4-ureidochroman-4-carboxylic acid, of the formula

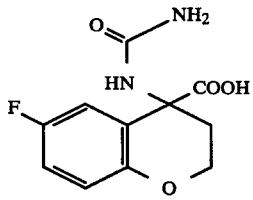

as either the D-(+)-(1-phenethyl)amine or the L-(−)-ephedrine salt, followed by simple cyclization in glacial acetic acid, provides an improved method for sorbinil. The racemic precursor is conveniently derived from the above racemic imidazolidine of the formula (II) via the amino acid of the formula

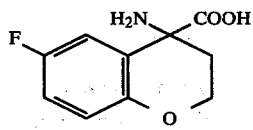

In this manner, outstanding yields of sorbinil are obtained with much lower solvent volumes and with readily available, relatively inexpensive optically active amines. At the same time the use of a highly toxic resolving agent is avoided. The efficiency of this process is further enhanced by isolating the undesired enantiomer from mother liquors and recycling to fresh racemate, via precursor 6-fluoro-4-chromanone.

Sorbinil has also been more recently prepared by an alternative synthesis in which the required chirality is induced during the synthetic sequence (Sarges, U.S. Pat. No. 4,286,098).

SUMMARY OF THE INVENTION

The present invention encompasses a process for the preparation of sorbinil, or a pharmaceutically acceptable cationic salt thereof, which comprises the steps of:

(a) separating a crystalline S-6-fluoro-4-ureidochroman-4-carboxylic acid with D-(+)-(1-phenethyl)amine or L-(−)-ephedrine, respectively of the formulae

from a racemic compound of the formula (III); and (b) cyclizing said phenethyl amine or ephedrine salt in excess glacial acetic acid to form said sorbinil.

Also within the purview of the present invention are the intermediate salts of S-6-fluoro-4-ureidochroman-4-carboxylic acid with either D-(+)-(1-phenethyl)amine or L-(−)-ephedrine.

DETAILED DESCRIPTION OF THE INVENTION

The process of the present invention is readily carried out. Racemic 6-fluoro-4-ureidochroman-4-carboxylic acid (available from 6-fluoro-4-chromanone by the method of Sarges, U.S. Pat. No. 4,130,714) is combined with D-(+)-(1-phenethyl)amine or L-(−)-ephedrine in a suitable solvent. Usually about mole for mole of acid and amine are employed, although the amount of amine can be varied from as little as 0.5 mole/mole to a large excess. To avoid precipitation of racemic free acid, it is preferred to employ at least about mole/mole. The solvent is usually organic in nature. With either amine, methanol is particularly well-suited. Acetone is also a preferred solvent when the amine is ephedrine. Simple experimentation will determine other solvents suitable for the present process. The salts are generally formed at elevated temperatures, e.g., 40°-100° C., conveniently between 40° C. and the reflux temperature of the solvent. It is not essential that complete solution occur at any stage, i.e., the salt can crystallize prior to complete solution of the starting racemic acid (III). The crystalline resolved salt is recovered after lowering the temperature, e.g., to 0°-40° C., and, if desired, digesting the product by stirring for 1 to 24 hours at the temperature used for isolation. If further purification of the resolved salt is desired, the initially recovered salt can be repulped or recrystallized from the same or another solvent, as delineated above.

The resolved salt, if desired, is converted to its acid form by standard techniques of acidification and extraction. The resolving agent, if desired, is recovered from the aqueous raffinate by standard techniques of basification and extraction.

The resolved free acid, or conveniently the amine salt itself, is readily converted to sorbinil by heating at 70°-110° C. in glacial acetic acid. This step is conveniently carried out over a steam bath at 90°-100° C.

The required racemic ureidocarboxylic acid (III) is prepared by total synthesis, e.g., conversion of 6-fluoro-4-chromanone to amino acid (IV) via the Strecker synthesis, followed by N-aminocarbonylation. It is preferable to prepare the intermediate amino acid (IV) from the racemic hydantoin (II), in turn readily prepared from 6-fluoro-4-chromanone in one step according to the method of Sarges, U.S. Pat. No. 4,130,714.

Conversion of the hydantoin (II) to the aminoacid (IV) is accomplished under a variety of aqueous, basic conditions. Suitable bases are sodium, potassium and barium hydroxide, used in excess (e.g., 2-4 moles of base/mole of hydantoin) in water at 75°-100° C., conveniently at reflux. The preferred base is sodium hydroxide, using about 4 moles of base/mole of hydantoin. The aminoacid can be recovered by neutralization or acidification and solvent displacement. Because the aminoacid is so highly water soluble, it is preferable to N-aminocarbonylate the amino acid in situ, i.e., without isolation. Thus the aqueous reaction mixture containing aminoacid is simply neutralized, preferably made slightly acidic, and treated with excess of an alkali metal cyanate. The resulting ureido derivative (III) is then readily precipitated by acidification.

The efficiency of the over-all process from 6-fluoro-4-chromanone to sorbinil is greatly increased by recovering crude enantiomer of the sorbinil precursor from mother liquors. Preferably also recovering the amine resolving agent, using standard techniques of basification and extraction, the enantiomeric material is recycled to 6-fluoro-4-chromanone, by the method of Cue, Massett and Hammen, U.S. Pat. application, Ser. No. 440,657, filed concurrently with present application, for "Regeneration of 6-Fluoro-4-Chromonone from By-products in the Synthesis of Sorbinil." This method is also disclosed by specific Examples below.

The present invention is illustrated by the following examples. However, it should be understood that the invention is not limited to the specific details of these examples. All temperatures are in °C. and are ambient unless otherwise specified. All solvent stripping was carried out in vacuo.

EXAMPLE 1

RS-4-Amino-6-fluorochroman-4-carboxylic Acid

A stirred slurry of RS-6-fluorospiro[chroman-4,4'-imidazolidine]-2',5'-dione, (78 g, 0.33 mole) and Ba-(OH)$_2$.8H$_3$O (208.3 g, 0.66 mole) in 585 ml H$_2$O was slowly heated to reflux over 3 hours and refluxed 16 hours. The slurry was cooled to 80° and powdered NH$_4$CO$_3$ (78 g) added portionwise over 5 minutes. Moderate foaming was noted. After stirring 1.5 hours at 80°, the mixture was cooled to 60° and filtered over diatomaceous earth with 2×100 ml hot H$_2$O for wash. The combined filtrate and washes were stripped to 200 ml and allowed to stand overnight. 2-Propanol (600 ml) was added and the mixture heated to 70° to dissolve precipitated solids. The hot solution was treated with activated carbon, filtered over diatomaceous earth and washed with hot 1:1 H$_2$O:2-propanol. The combined filtrate and washes were stripped to 200 ml, and water chased with 3×300 ml fresh 2-propanol. The resulting thick slurry was diluted with 200 ml additional 2-propanol, cooled to 5°, granulated 0.5 hour, filtered and air dried to yield title product, 63.6 g, 91.2%, mp 252-253 (dec.).

EXAMPLE 2

RS-6-Fluoro-4-ureidochroman-4-carboxylic Acid

Method A

Title product of the preceding Example (21.1 g, 0.1 mole) was slurried in 250 ml H$_2$O. KOCN (16.2 g, 0.2 mole) was added portionwise over 2.5 minutes. The almost complete solution was stirred 22 hours at 23°, during which the pH increased from 6.8 to 9.1 and complete solution occurred. Concentrated HCl (19.0 ml) was added over 1 hour, keeping temperature 25°-29° C. The resulting slurry was granulated 1 hour (pH 3.2-3.5), and title product recovered by filtration with 150 ml H$_2$O wash, partially dried in air and then for 18 hours at 50°-55° in vacuo, 20.0 g, 79%.

Method B

The same starting imidazolidine used in the preceding Example (47.2 g, 0.2 mole) and NaOH pellets (28 g, 0.7 mole) were combined in 600 ml H$_2$O and heated at reflux for 40 hours. The reaction mixture was cooled to 24° and the pH lowered from 11.8 to 5.0 with 6N HCl. Gassing was noted below pH 8. After stirring the slurry for 20 minutes at pH 5, KOCN (32.5 g, 0.4 mole) was added over 2 minutes, the mixture stirred 20 hours and a small amount of solids removed by filtration with 50 ml water for wash. The combined filtrate and wash was adjusted from pH 8.5 to 4.0 with 6N HCl. Precipitated title product was recovered by filtration, washed with warm water and air dried, 39.7 g (78%), mp 198-199 (dec.).

Alternatively the NaOH hydrolysis stage was carried out at 118° and 27 psig for 18 hours. Further reaction with KOCN and isolation as immediately above likewise gave title product, 38.8 g (76.4%), mp 199-200 (dec.).

Alternatively KOH (26.4 g, 85%, 0.4 mole) was substituted for NaOH, with a reflux time of 22 hours. Reaction with KOCN and isolation as immediately above likewise gave title product, 36.8 g (72.4%), mp 198-199 (dec.).

EXAMPLE 3

D-(+)-(1-Phenethyl)ammonium S-6-Fluoro-4-ureidochroman-4-carboxylate

Title product of the preceding Example (10.0 g, 39.4 mmole) was slurried in 400 ml of methanol at 45°±5° for 1 hour. Over 4 minutes 4.87 g, (40.1 mmole) of D-(+)-(1-phenethyl)amine in 45 ml methanol was added to the resulting thin slurry, yielding a solution. The bath was removed, the mixture cooled slowly to ambient temperature, the mixture granulated for 16 hours, and crude title product recovered by filtration and dried at 60° in air, 6.4 g, 86.6%, mp 206°-210°, [alpha]$_D^{25}$=+54.3° (c=0.3, methanol). Crude title product, 6 g, was repulped in 180 ml methanol at 40°-50° for 1 hour, cooled to ambient temperature, granulated 3 hours, filtered and air dried to yield purified title product, 4.4 g, mp 214°-216°, [alpha]$_D^{25}$=+69° (c=0.3 in methanol), 73.3% recovery, overall 63.5% yield.

The mother liquor from crude title product was stripped to yield a mixture consisting primarily of D-(+)-(1-phenethyl)ammonium R-6-fluoro-4-ureidochroman-4-carboxylate together with title product, 8.3 g, mp 198°–200° C., $[\alpha]_D^{25} = -35.4°$ (c=0.5, methanol), suitable for recycle to 6-fluoro-4-chromanone. Under one option, this salt mixture is distributed between ethyl acetate and water, with the pH first adjusted to 10. The ethyl acetate layer is separated and optically active amine recovered by evaporation. The pH of the aqueous phase is then adjusted to 1–2 with hydrochloric acid and extracted with fresh ethyl acetate. The organic phase is washed with additional small portions of water, dried (MgSO4) and evaporated to yield a mixture of R and RS-6-fluoro-4-ureidochroman-4-carboxylic acid.

EXAMPLE 4

Sorbinil

Title product of the preceding Example (4.3 g, 11 mmoles) was slurried in 30 ml glacial CH3CO2H at 93° C. for 2 hours, a solution resulting after the initial 15 minutes. The mixture was cooled to 60° and stripped to 10 ml. Warm water (21.5 ml, 50°) was added, resulting in a slurry having pH 3.5. After 5 minutes, the pH was adjusted to 4.5 with 4 ml 4N NaOH (temperature now 28°) and the mixture cooled to 20° over 30 minutes. Filtration gave relatively pure sorbinil directly, 2.35 g, 90.3%, mp 238–241° C., $[\alpha]_D^{25} = +52.7°$ (c=1, methanol). Sorbinil was purified by dissolving 2.2 g in 27.4 ml boiling acetone, clarified by hot filtration and the mother liquor stripped to 13 ml. The resulting slurry was twice slowly diluted with 17.2 ml of hexane and stripped to 13 ml. Filtration and air drying gave purified sorbinil, 1.924 g, 87.5%, mp 239.5°–242.5°, $[\alpha]_D^{25} = +54.5$ (c=1, methanol).

Relatively pure sorbinil, 56.2 g, mp 237°–241°, $[\alpha]_D^{25} = +52.3°$ (c=1, methanol), prepared in like manner in 89.8% yield from title product of the preceding Example was dissolved in 700 ml of boiling acetone, clarified by filtration and stripped to 300 ml. Hexane (400 ml) was slowly added and the mixture restripped to 300 ml. Hexane addition and stripping was repeated, yielding purified title product, vacuum dried at 40° C. for 18 hours, 54.9 g, 97.7%, mp 236°–241°, $[\alpha]_D^{25} = +53.4°$ (c=1 in methanol).

EXAMPLE 5

L-(−)Ephedrine Salt of S-6-fluoro-4-ureidochroman-4-carboxylic Acid

Method A

Title product of Example 2 (35.6 g, 0.14 mole) was slurried 1.07 liters acetone, stirred at reflux (59°) for 30 minutes, and cooled to 54°. L-(−)-ephedrine (24.4 g, 0.148 mole) was added in one portion. The slurry thinned and near solution resulted. After less than 2 minutes at 55° rapid crystallization began. The slurry was refluxed 2 hours, cooled to 40° C. and sugarlike crystals of crude title product recovered by filtration, 26.1 g; mp 204° (dec.); $[\alpha]_D^{25} = +37.0$ (c=1, methanol).

Mother liquor at ambient temperature gave a second crop of solids, 1.3 g, mp 180°–185° (dec); $[\alpha]_D^{25} = 0$ (c=1, methanol).

Concentration of mother liquor gave foamy solids, 32.9 g, mp 72°–90° (dec.); $[\alpha]_D^{25} = -55.7°$ (c=1, methanol).

First crop solids (25 g) were repulped in 250 ml of refluxing acetone, recovered after cooling to 40°, 24 g; mp 205° (dec.); $[\alpha]_D^{25} = +38.2$ (c=1, methanol).

Evaporation of mother liquor to dryness gave 1.2 g, mp 90°–110° (dec.); $[\alpha]_D^{25} = +31.4°$ (c=1, methanol).

Once repulped solids (13 g) were repulped in 260 ml of refluxing acetone, recovered after cooling to 45°, 11.7 g, $[\alpha]_D^{25} = +39.3$ (c=1, methanol). Evaporation of mother liquor gave an additional 1.1 g of solids.

Method B

Title product of Example 2 (100 g) was stirred at reflux (65°) in 374 ml methanol for 30 minutes, then cooled to 59°. Water (7.42 ml) and L-(−)-ephedrine (68 g) were added, resulting in heavy precipitation. The slurry was refluxed at 66° for 45 minutes, cooled to 27° and highly purified title product directly recovered by filtration, 70.4 g, $[\alpha]_D^{25} = +44.36$ (c=1.04 in methanol). The filtrate was evaporated to yield the crude diastereomeric salt, L-(−)-ephedrine R-6-fluoro-4-ureidochroman-4-carboxylate, 116.3 g.

EXAMPLE 6

Sorbinil

Once repulped title product of the preceding Example (9.6 g.; made by Method A) and 68 ml. glacial CH3CO2H were heated at 95° C. for 1 hour, evaporated in vacuo at 60° to 20 g. of oily residue, diluted with 50 ml. H2O at 60°, and then 50 ml. H2O at 10°. The resulting slurry was adjusted from pH 3 to 4.5 with 4N NaOH to yield crude sorbinil, 4.7 g., mp 234°–240°; $[\alpha]_D^{25} = +50.5$ (c=1, methanol). This crude sorbinil, 4.0 g., was dissolved in 60 ml. boiling absolute ethanol, clarified by filtration, cooled to 24° and purified sorbinil recovered by filtration, 2.0 g., mp 240.5–243.0, $[\alpha]_D^{25} = +55.4$ (c=1, methanol).

By the same method the highly purified title product of the preceding Example (10 g.; made by Method B) was converted to highly pure sorbinil, 4.93 g.; mp 240°–242°; $[\alpha]_D^{25} = +54.7°$ (c=1, methanol).

EXAMPLE 7

R- and RS-6-Fluorospiro-[chroman-4,4′-Imidazolidine]-2′,5′-dione

By the procedure of Example 4, D-(+)-1-(phenethyl)amine salt of R- and RS-6-fluoro-4-ureidochroman-4-carboxylic acid is converted to title product.

EXAMPLE 8

Crude 6-Fluoro-4-Chromanone from Sorbinil Enantiomer and Racemate

Levorotatory (R-) and/or racemic (RS-) 6-fluorospiro-[chroman-4,4′-imidazolidine]-2′, 5′-dione (100 g, 0.423 mmole) was slurried in 750 ml H2O. Ba(OH)2.8H2O (267.0 g, 0.846 mole) was added and the resulting thin slurry refluxed 48 hours. The resulting heavy suspension was cooled to 60°–65° and NH4CO3 (100 g, 0.876 mole) added. The slurry was then stirred 30 minutes and filtered at 50°–55° with 300 ml of warm water wash of the collected inorganic salts. The combined filtrate and wash was adjusted from pH 8.5 to 4.5–5.0 with hydrochloric acid. To the acidified solution, N-chlorosuccinimide (57.0 g, 0.427 mole) was added portionwise over 5 hours at 30–45 minute intervals. The resulting slurry was stirred 17 hours at room temperature, then 1 hour at 15°. Solids were recovered by filtration, taken up in CH2Cl2, treated with activated carbon, and CH2Cl2 displaced with hexane to a pot temperature of 68°–69° and a final volume of 400–500 ml, during which crystallization occurred. After cooling and digestion for 1 hour at 20°–25°, purified title product was recovered by filtration, 50.2 g, having the physical properties of the known material.

Title product prepared in this manner contains 6-fluoro-4-chloriminochroman as an impurity. The latter interferes with further use of title product in the synthesis of additional sorbinil. Said impurity is removed (being converted to the desired 6-fluoro-2-chromanone) according to the following Example.

EXAMPLE 9

Purification of Crude 6-Fluoro-4-chromanone by Hydrogenation

Crude 6-fluoro-4-chromanone, containing 6-fluoro-4-chloriminochroman as an impurity (5.0 g), 5% Pd/C (50% water wet, 0.25 g), and 1:1 $H_2O:C_2H_5OH$ (100 ml) were combined and the mixture hydrogenated at 45 psig of hydrogen (4 atmospheres) for 2 hours, by which time tlc on silica gel (using toluene:methyl ethyl ketone: acetic acid 5:2:1 as eluant) indicated absence of faster moving chlorimine ($R_f$ 0.8) in the 6-fluoro-4-chromanone ($R_f$ 0.7). The reaction mixture was diluted with 100 ml of methanol (to completely dissolve solids other than catalyst), the catalyst recovered by vacuum filtration on a pad of diatomaceous earth, and the filtrate evaporated in vacuo to 50 ml (from a water bath at 45°), cooled to 5°, granulated for 15 minutes and filtered to yield purified title product, 2.65 g, mp 108°–112°, tlc as indicated above.

EXAMPLE 10

R- and RS-6-Fluoro-4-ureidochroman-4-carboxylic Acid

Method A

Recovered D-(+)-(1-phenethyl)ammonium R-6-fluoro-4-ureidochroman-4-carboxylate (containing also in minor portion the corresponding D-ammonium S-carboxylate salt), 32.3 g, was combined with 215 ml of 1N HCl and stirred at 16°–23° for 21 hours. Title product was recovered by filtration, 20.6 g, 94%, mp 195°–198° (dec.).

Method B

A column containing a 50 ml volume of previously used ion exchange resin (Amberlite IRA 900) was slowly flushed sequentially with 250 ml deionized $H_2O$, 250 ml 1N NaOH, 250 ml $N_2$ sparged $H_2O$ and 250 ml $N_2$ sparged methanol. Crude enantiomeric salt (10 g) in 50 ml methanol was placed on the column, eluted with an additional 100 ml of methanol, and the eluant evaporated in vacuo to yield recovered ephedrine, 0.0199 mole, by titrimetric assay with 0.1N HCl in methanol. The column was then eluted with 150 ml of methanol containing 4.4 g dry HCl and finally with 150 ml of fresh methanol. The latter methanol HCl and methanol eluants were combined and evaporated in vacuo to yield enantiomeric (R) and racemic (RS) 6-fluoro-4-ureidochroman-4-carboxylic acid, 5.86 g.

EXAMPLE 11

Crude 6-Fluoro-4-chromanone from R- and RS-6-Fluoro-4-ureidochroman-4-carboxylic Acid Title product of the preceding Example (100 g) was slurried in 475 ml $H_2O$. 50% NaOH, 32 g, was added, producing incomplete solution. The mixture was warmed over 40 minutes to a pot temperature of 100° (reflux), by which time there was complete dissolution. Reflux was continued 18 hours and the mixture cooled. The pH was 9.6 and tlc indicated incomplete reaction. The pH was increased to 12.0 with 13.8 g of 50% NaOH and the mixture reheated to reflux for 2.5 hours, at which time tlc on silica gel (toluene:methyl ethyl ketone:acetic acid 5:2:1 as eluant) indicated no more than traces of starting material ($R_f$ 0.5) with high level of intermediate R- and RS-6-fluoro-4-aminochroman-4-carboxylic acid ($R_f$ 0.0). The reaction mixture was cooled to 20° and, maintaining temperature less than 30°, adjusted to pH 4.5 with concentrated HCl, as a precipitate formed. N-chlorosuccinimide (53 g) was added over 15 minutes, maintaining temperature less than 30° C. and the pH 4.0–4.5 by the simultaneous addition of 7 ml of 50% NaOH. The reaction mixture was stirred 1 hour at 25° C., by which time the pH was 5.2 and tlc (above system) indicated complete conversion of intermediate amino acid to products. The pH was then adjusted to 9.6 with about 27 ml of 50% NaOH, the basic slurry granulated for 2 hours at 20°, and title product recovered by filtration, 50.0 g, mp 55°–58° (partial) 65°–75° (complete, but melt not clear); tlc (above system) indicated title product ($R_f$ 0.7) containing 6-fluoro-4-chloroiminochroman ($R_f$ 0.8).

Alternatively, D-(+)-(1-phenethyl)ammonium R-6-fluoro-4-ureidochroman-4-carboxylate, containing in minor portion the corresponding D-ammonium S-carboxylate is used in the present process. In the initial stage of the process, the salt is distributed between the 50% NaOH and an equal volume of $CH_2Cl_2$. The aqueous phase is washed 2 x with one third volume of $CH_2Cl_2$. The organic layers are combined and stripped to yield D-(+)-(1-phenethyl)amine suitable for recycling. The aqueous phase is carried through the balance of the present process to yield title product.

EXAMPLE 12

6-Fluoro-4-Chloriminochroman from R- and RS-6-fluoro-4-ureidochroman

The preceding Example was repeated on one tenth scale to obtain intermediate R- and RS-6-fluoro-4-aminochroman-4-carboxylic acid in NaOH solution. To the solution was added (dropwise) 15% w/w NaOCl (48.2 ml), maintaining temperature 20°–25°. The mixture was stirred 3.5 hours at 20°–25°, by which time tlc (system as in preceding Example) indicated conversion of amino acid to essentially clean title product, with light trace of 6-fluoro-4-chromanone. Title product was recovered by filtration, 3.8 g, $R_f$ 0.8 in above system.

EXAMPLE 13

6-Fluoro-4-chromane from Chlorimine

Title product of the preceding Example (3.6 g) and 5% Pd/C, 50% water wet (0.18 g dry basis) were combined in 72 ml of methanol:water 9:1. The pH was adjusted to 2.0 with concentrated HCl and the mixture hydrogenated at 40–45 psig (3.7–4 atmospheres) of hydrogen for 2 hours. Catalysts was recovered by filtration on a pad of diatomaceous earth. The filtrate showed only title product by tlc ($R_f$ 0.7 in system of immediately preceding Examples), readily recovered by evaporation in vacuo. Tlc indicated some product was retained on the catalyst cake, readily recovered by repulp of the catalyst cake in methanol.

What is claimed is:

1. A process for the preparation of a crystalline S-6-fluoro-4-ureidochroman-4-carboxylic acid salt with D-(+)-(1-phenethyl)amine or L-(—)-ephedrine which comprises combining a racemic compound of the formula

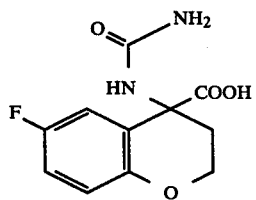

with at least a half molar quantity of D-(+)-(1-phenethyl)amine or L-(—)-ephedrine in a reaction-inert organic solvent and recovering said crystalline salt.

2. A process of claim 1 which further comprises cyclization of said recovered crystalline salt in glacial acetic acid to form sorbinil and recovering said sorbinil or a pharmaceutically-acceptable cationic salt thereof.

3. A process of claim 1 wherein the amine is L-(—)-ephedrine.

4. A process of claim 2 wherein the amine is L-(—)-ephedrine.

5. A process of claim 1 wherein the amine is D-(+)-1-(phenethyl)amine.

6. A process of claim 2 wherein the amine is D-(+)-1-(phenethyl)amine.

7. A process of claim 1 wherein the organic solvent is methanol.

8. A process of claim 3 wherein the organic solvent is acetone.

* * * * *